(12) United States Patent
Shiina et al.

(10) Patent No.: US 7,338,452 B2
(45) Date of Patent: Mar. 4, 2008

(54) ULTRASONIC DIAGNOSTIC APPARATUS AND METHOD

(75) Inventors: Tsuyoshi Shiina, Tsukuba (JP); Naotaka Nitta, Tsukuba (JP); Hiroyuki Yagami, Fuji (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 529 days.

(21) Appl. No.: 10/839,205

(22) Filed: May 6, 2004

(65) Prior Publication Data

US 2005/0004467 A1   Jan. 6, 2005

(30) Foreign Application Priority Data

May 7, 2003   (JP)   ............................. 2003-129173

(51) Int. Cl.
*A61B 8/12* (2006.01)
(52) U.S. Cl. .................................................... 600/467
(58) Field of Classification Search ........ 600/463–471, 600/438; 128/916; 73/37, 37.5, 573–4, 73/78, 760, 763, 778, 789, 801, 807
See application file for complete search history.

(56) References Cited

U.S. PATENT DOCUMENTS

| 5,107,837 | A | | 4/1992 | Ophir et al. |
| 5,125,410 | A | | 6/1992 | Misono et al. |
| 5,411,028 | A | * | 5/1995 | Bonnefous ................... 600/454 |
| 5,495,771 | A | | 3/1996 | Sumi et al. |
| 5,524,636 | A | * | 6/1996 | Sarvazyan et al. ........... 600/587 |
| 6,099,471 | A | | 8/2000 | Torp et al. |
| 6,165,128 | A | | 12/2000 | Cespedes et al. |
| 6,270,459 | B1 | | 8/2001 | Konofagou et al. |
| 7,074,188 | B2 | * | 7/2006 | Nair et al. ................... 600/443 |
| 7,175,597 | B2 | * | 2/2007 | Vince et al. ................. 600/443 |
| 2004/0167403 | A1 | * | 8/2004 | Nightingale et al. ........ 600/437 |

FOREIGN PATENT DOCUMENTS

| JP | 05-317313 | 12/1993 |
| JP | 08-010260 | 1/1996 |
| JP | 2000-229078 | 8/2000 |

(Continued)

OTHER PUBLICATIONS

Tsuyoshi Shiina et al., "Real Time Tissue Elasticity Imaging Using the Combined Autocorrelation Method", J Med Ultrasonics, vol. 29, Autumn (2002), pp. 119-128.

(Continued)

*Primary Examiner*—Francis J. Jaworski
(74) *Attorney, Agent, or Firm*—Buchanan Ingersoll & Rooney PC

(57) ABSTRACT

An ultrasonic diagnostic system according to the present invention has an ultrasonic transducer mounted on a catheter, an instantaneous distortion value calculator which calculates an instantaneous distortion value at the location to be evaluated in the blood vessel based on received signal representative of received reflection by the ultrasonic transducer, an analyzer which analyzes a state of the location to be evaluated using time-series data of instantaneous distortion values which are calculated at a plurality of times in a chronological sequence by the distortion value calculator, and a display which displays an analyzed result produced by the analyzer.

53 Claims, 8 Drawing Sheets

FOREIGN PATENT DOCUMENTS

| | | |
|---|---|---|
| JP | 3182479 | 4/2001 |
| WO | WO 98/23210 | 6/1998 |
| WO | 2004/010872 A1 | 12/2004 |

OTHER PUBLICATIONS

Tsuyoshi Shiina et al., "Coronary Artery Characterization Based on Tissue Elasticity Imaging -in vivo Assessment-", 2002 IEEE Ultrasonics Symposium, (2002), pp. 1855-1858.

Naotaka Nitta et al., "Estimation of Nonlinear Elasticity Parameter of Tissues by Ultrasound", Jpn. J. Appl. Physi., vol. 41 (2002), pp. 3572-3578.

Makoto Yamakawa et al., "Strain Estimation Using the Extended Combined Autocorrelation Method", Jpn. J. Appl. Phys. vol. 40 (2001), pp. 3872-3876.

Chris L. De Korte et al., "Influence of Catheter Position on Estimated Strain in Intravascular Elastography", IEEE Transactions on Ultrasonics, Ferroelectrics, and Frequency Control, vol. 46, No. 3, May 1999, pp. 616-625.

T. Varghese et al., "Noise Reduction in Elastograms Using Temporal Stretching with Multicompression Averaging", Ultrasound in Medicine and Biology, USA, vol. 22, No. 8, 1996, pp. 1043-1052.

N. Nitta et al, "Tissue Elasticity Reconstruction Based on Three-Dimensional Displacement Data Estimated by the Weighted Phase Gradient Method", 1999 IEEE Ultrasonics Symposium Proceedings International Symposium, USA, vol. 2, 1999, pp. 1665-1668.

European Patent Office Search Report.

European Patent Office Communication Pursuant to Article 96(2) EPC.

\* cited by examiner

ULTRASONIC DIAGNOSTIC APPARATUS AND METHOD

This application is based on Japanese Patent Application No. 2003-129173 filed on May 7, 2003, the contents of which are hereby incorporated by reference.

BACKGROUND OF THE INVENTION

1. Field of the Invention

The present invention relates to an ultrasonic diagnostic apparatus and method for analyzing an intravascular state, and more particularly to an ultrasonic diagnostic apparatus and method for diagnosing the property and state of an intravascular sclerotic nidus called "plaque" according to an intravascular echoing process.

Signs and symptoms that result in an observation of acute ischemia, such as unstable angina and acute myocardial infarction, are called acute coronary syndrome. Heretofore, it has been considered that the acute coronary syndrome is caused by a constriction or obstruction in a blood vessel that is produced by a gradual accumulation of plaque (sclerotic nidus) within the blood vessel over many years.

In recent years, however, a certain type of plaque that is formed in a blood vessel is thought to be responsible for the development of acute coronary syndrome. Generally, a plaque comprises a soft atheromatous lipid component and a relatively hard fibrous capsule (fibrous component). A plaque having a higher lipid content is a vulnerable plaque that can easily be broken by even a small stimulus. A plaque having a lower lipid content is a plaque that is less liable to be broken. The vulnerable plaque with the higher lipid content is softer and more deformable than the plaque with the lower lipid content. The former plaque is called a soft plaque, whereas the latter plaque is called a hard plaque. When the vulnerable soft plaque is broken, it produces a thrombus, causing a constriction or obstruction in the blood vessel which tends to bring about the acute coronary syndrome.

For preventing and appropriately treating the acute coronary syndrome, it is necessary to establish a technique to evaluate the property and state of plaques. Particularly, there is a need for adequately determining whether a plaque formed in a blood vessel is a vulnerable soft plaque or a hard plaque.

For determining the property and state of plaques, it is better to use an intravascular echoing process than to use an X-ray angiographic process. According to the intravascular echoing process, a catheter having an ultrasonic probe on its end is inserted into a blood vessel. The ultrasonic probe transmits an ultrasonic wave while circumferentially scanning a location to be evaluated (radial scanning), and receives a reflected wave to produce a received signal. The amplitude of the received signal is modulated in luminance to produce a tomographic image of the blood vessel at the evaluated location.

In actual clinic sites, the property and state of a plaque in the blood vessel are analyzed based on the produced tomographic image to regard a region of high luminance as a fibrous component of the plaque and also to regard a region of low luminance as a lipid component of the plaque. For example, a plaque containing 80% or more of a region of high luminance is regarded as a hard plaque, and a plaque containing 80% or more of a region of low luminance is regarded as a soft plaque. In this manner, a pseudo evaluation of the property and state of plaques is made.

However, the direct relationship between luminance and plaque state is not strong enough. It is difficult to analyze the property and state of plaques accurately in detail according to the analyzing process based solely on luminance. There has been a demand for a technique to directly analyze the property and state of plaques by determining dynamic characteristics of plaques. To meet such a demand, there have been proposed various techniques to determine dynamic characteristics of plaques, such as a distortion value and a modulus of elasticity, using ultrasonic energy Japanese Patent Laid-open No. 2000-229078 discloses a technique for tracking the position of a location to be evaluated in a blood vessel, calculating the modulus of elasticity of the wall of the blood vessel, and evaluating the property and state of a plaque in the blood vessel.

Japanese Patent Laid-open No. Hei 8-10260 discloses a technique for allocating partial regions of two images obtained at respective two times, determining a complex conjugate product, determining a displacement from the gradient of the phase of the complex conjugate product, and evaluating the rigidity of a tissue in an examined sample.

Japanese Patent Laid-open No. Hei 5-317313 reveals a technique for calculating the absolute modulus of elasticity at a location to be evaluated in a blood vessel based on a change in the distance between two particular points and the blood pressure in the blood vessel. This document also discloses a technique for displaying a tomographic image of a blood vessel with a different hue added depending on the difference between the moduli of elasticity that are determined at respective locations to be evaluated in the blood vessel.

Japanese Patent No. 3182479 reveals a technique for determining a displaying a ratio of moduli of elasticity (indirect modulus of elasticity) which represent respective elastic levels at an observed point and a reference point, rather than calculating an absolute modulus of elasticity.

The above conventional techniques calculate a distortion value and/or a modulus of elasticity to evaluate the hardness of a location to be evaluated in a blood vessel. Actually, the distortion values of a blood vessel wall and a plaque change periodically because the cross-sectional area of the lumen of the blood vessel changes periodically due to blood pressure changes caused by cardiac beats. Specifically, when the blood vessel is contracted and expanded, the distortion values change greatly, and when the blood vessel switches from a contracted state to an expanded state and also from an expanded state to a contracted state, the distortion values do not change significantly.

The blood vessel wall and the plaque are essentially elastic bodies that are dynamically nonlinear. Stresses in the blood vessel wall and the distortion values are nonlinearly related to each other. Because of the nonlinearity, the moduli of elasticity of the blood vessel wall and the plaque change with time depending on the contracted and expanded stages of the blood vessel. In addition, since the blood vessel wall and the plaque are viscous, they need to be treated as viscoelastic bodies.

The conventional techniques referred to above do not analyze the state of a location to be evaluated based on a time-dependent change of a chronological sequence of distortion values and moduli of elasticity. Therefore, it has been impossible with the conventional techniques to analyze the state of a location to be evaluated, i.e., the property and state of a plaque, in view of the dynamic nonlinearity and viscoelasticity of the blood vessel wall and the plaque.

SUMMARY OF THE INVENTION

It is an object of the present invention to provide an ultrasonic diagnostic apparatus and method for analyzing the state of a location to be evaluated in view of the nonlinearity and viscoelasticity of the location, based on time-series data of instantaneous distortion values at a plurality of times.

Another object of the present invention is to provide an ultrasonic diagnostic apparatus and method for analyzing the state of a location to be evaluated in view of the nonlinearity and viscoelasticity of the location, based on time-series data of instantaneous moduli of elasticity at a plurality of times.

According to an aspect of the invention, an ultrasonic diagnostic apparatus has an insert to be inserted into a blood vessel, an ultrasonic transducer mounted on the insert for transmitting an ultrasonic wave in the blood vessel, receiving a reflection of the ultrasonic wave, and producing a received signal representative of the received reflection, a distortion value calculator which calculates an instantaneous distortion value at a location to be evaluated in the blood vessel based on the received signal, an analyzer which analyzes a state of the location to be evaluated using time-series data of instantaneous distortion values which are calculated at a plurality of times in a chronological sequence by the distortion value calculator, and a display which displays an analyzed result produced by the analyzer.

According to another aspect of the invention, an ultrasonic diagnostic apparatus has an insert to be inserted into a blood vessel, an ultrasonic transducer mounted on the insert for transmitting an ultrasonic wave in the blood vessel, receiving a reflection of the ultrasonic wave, and producing a received signal representative of the received reflection, a modulus-of-elasticity calculator which calculates an instantaneous modulus of elasticity at a location to be evaluated in the blood vessel based on the received signal, an analyzer which analyzes a state of the location to be evaluated using time-series data of instantaneous moduli of elasticity which are calculated at a plurality of times in a chronological sequence by the modulus-of-elasticity calculator, and a display which displays an analyzed result produced by the analyzer.

According to still another aspect of the invention, an ultrasonic diagnostic method has a step of transmitting an ultrasonic wave in a blood vessel, receiving a reflection of the ultrasonic wave, and producing a received signal representative of the received reflection, a step of calculating an instantaneous distortion value at a location to be evaluated in the blood vessel based on the received signal, a step of analyzing a state of the location to be evaluated using time-series data of instantaneous distortion values which are calculated at a plurality of times in a chronological sequence, and a step of displaying an analyzed result produced.

According to a further aspect of the invention, an ultrasonic diagnostic method has a step of transmitting an ultrasonic wave in a blood vessel, receiving a reflection of the ultrasonic wave, and producing a received signal representative of the received reflection, a step of calculating an instantaneous modulus of elasticity at a location to be evaluated in the blood vessel based on the received signal, a step of analyzing a state of the location to be evaluated using time-series data of instantaneous moduli of elasticity which are calculated at a plurality of times in a chronological sequence, and a step of displaying an analyzed result produced.

The above and other objects, features, and advantages of the present invention will become apparent from the following description when taken in conjunction with the accompanying drawings which illustrate preferred embodiments of the present invention by way of example.

DETAILED DESCRIPTION OF THE PREFERRED EMBODIMENTS

1st Embodiment

Figure 1:
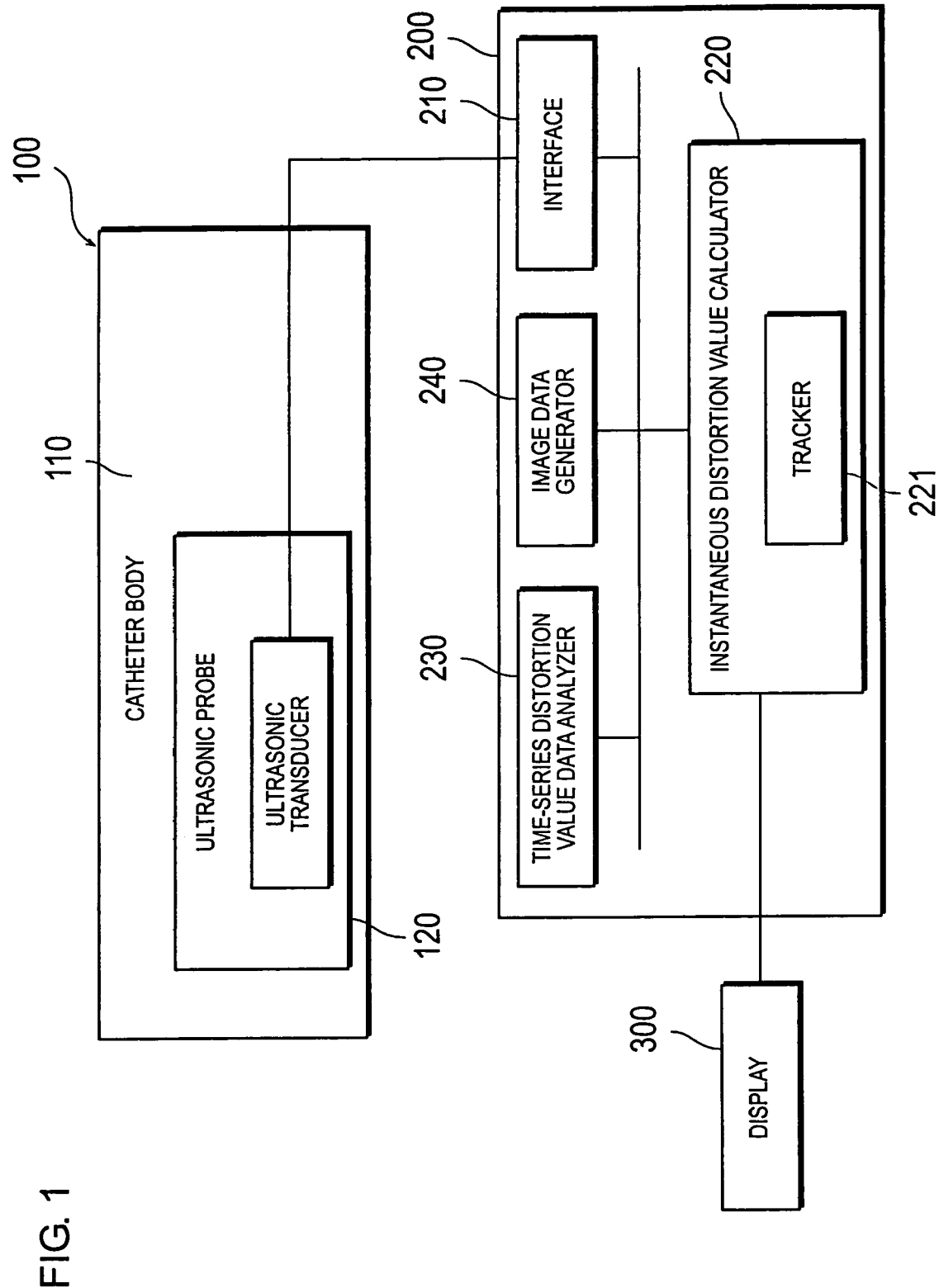
FIG. 1 is a block diagram of an ultrasonic diagnostic system according to a first embodiment of the present invention.

FIG. 1 shows in block form an ultrasonic diagnostic system according to a first embodiment of the present invention.

As shown in FIG. 1, the ultrasonic diagnostic system according to the first embodiment generally comprises an ultrasonic catheter 100, a controller 200, and a display 300.

The ultrasonic catheter 100 comprises a catheter body (insert) 110 that can be inserted into a blood vessel and an ultrasonic probe 120 mounted in the catheter body 110. The ultrasonic probe 120 is disposed in a lumen in the catheter body 110, and acts as an ultrasonic transmitter/receiver for transmitting and receiving an ultrasonic wave in the blood vessel. Specifically, the ultrasonic probe 120 is an acoustic transducer and alternately repeats the transmission and reception of ultrasonic waves, so that the single ultrasonic probe 120 can transmit and receive ultrasonic waves. The ultrasonic probe 120 may alternatively comprise an ultrasonic transmitting part and an ultrasonic receiving part as separate elements.

With the ultrasonic catheter 100 inserted in a location to be evaluated in the blood vessel, the ultrasonic probe 120 transmits an ultrasonic wave while making radial scanning electronically or mechanically, i.e., rotating circumferentially, and converts an ultrasonic wave reflected from the blood vessel wall into an electric signal, i.e., a received signal (echo signal). Since the ultrasonic probe 120 receives the reflected ultrasonic wave while making radial scanning, the ultrasonic probe 120 can produce data (two-dimensional data) of a tomographic image of the blood vessel perpendicularly across the longitudinal axis of the blood vessel. The ultrasonic diagnostic system according to the first embodiment may also move the ultrasonic probe 120 for scanning along the longitudinal axis of the blood vessel, in addition to the radial scanning, for producing three-dimensional volume data representative of a three-dimensional shape of the blood vessel. The ultrasonic catheter 100 itself has a structure which is identical to the structure of conventional ultrasonic catheters, and will not be described in detail below.

When the ultrasonic probe 120 applies an ultrasonic wave to a blood vessel wall or a plaque, the ultrasonic wave is reflected in the blood vessel wall or the plaque, and then received by the ultrasonic probe 120. Since the blood vessel wall or the plaque is locally deformed and distorted in response to cardiac beats, the distance between two points in an object to be evaluated, i.e., the blood vessel wall or the plaque, changes before and after it is deformed in response to cardiac beats. Therefore, the waveform of the received ultrasonic wave locally moves due to the change in the distance between the two points in the object to be evaluated in response to cardiac beats.

The controller 200 will be described below. The controller 200 may comprise a personal computer or a computer such as a work station. The controller 200 has an interface 210, an instantaneous distortion value calculator 220, a time-series distortion value data analyzer 230, and an image data generator 240.

The interface 210 comprises an interface for acquiring a received signal produced by the ultrasonic catheter 100. The interface 210 according to the present embodiment captures a received signal, which has been produced by radial scanning with ultrasonic waves, over a period of time comprising at least a plurality of cardiac beats.

The instantaneous distortion value calculator 220 calculates instantaneous distortion values at the location to be evaluated in the blood vessel. Specifically, the instantaneous distortion value calculator 220 calculates an instantaneous distortion value at each point of time when the blood vessel is contracted and expanded by cardiac beats. The instantaneous distortion value calculator 220 calculates an instantaneous distortion value in each sampling period which is shorter than the period of cardiac beats, and performs such calculations over a plurality of cardiac beats. In this manner, the instantaneous distortion value calculator 220 produces time-series data of instantaneous distortion values (hereinafter referred to as "time-series distortion value data") at a plurality of times which are calculated in a chronological sequence. The instantaneous distortion value calculator 220 has a tracker 221 for tracking the position of the location to be evaluated in the blood vessel. The tracker 221 tracks the position of the location to be evaluated in the blood vessel according to an autocorrelation process or a composite autocorrelation process. Details of the tracker 221 will be described later.

The time-series distortion value data analyzer 230 analyzes the state of the location to be evaluated, based on the time-series distortion value data produced by the instantaneous distortion value calculator 220. The time-series distortion value data analyzer 230 determines whether the plaque in the location to be evaluated is a soft plaque or a hard plaque based on the dynamic nature of the plaque. Stated otherwise, the time-series distortion value data analyzer 230 evaluates the proportion of a lipid component of the plaque based on the dynamic nature of the plaque.

That the state of the location to be evaluated is analyzed based on the time-series distortion value data which includes information about the dynamic nonlinearity and viscoelasticity of the location to be evaluated, such as a blood vessel wall or a plaque, constitutes a feature of the ultrasonic diagnostic system according to the present embodiment. The time-series distortion value data analyzer 230 should preferably have a first function to divide the time-series distortion value data into a plurality of frequency components and analyze the state of the location to be evaluated based on the intensity of a certain one of the frequency components, and a second function to analyze the state of the location to be evaluated based on a phase lag (which may be a phase lead) of the time-series distortion value data. However, the time-series distortion value data analyzer 230 may have either the first function or the second function. The time-series distortion value data analyzer 230 can also calculate a rate of time-dependent change of the distortion value to analyze the location to be evaluated. Details of the functions of the time-series distortion value data analyzer 230 will be described later.

The image data generator 240 generates tomographic image data of the blood vessel based on the received signal from the interface 210. If the ultrasonic diagnostic system moves the ultrasonic probe 120 for scanning along the longitudinal axis of the blood vessel, in addition to the radial scanning, then the image data generator 240 generates three-dimensional volume data in the blood vessel. The image data generator 240 also generates image data representative of the analyzed results produced by the time-series distortion value data analyzer 230.

The instantaneous distortion value calculator 220, the time-series distortion value data analyzer 230, and the image data generator 240 are implemented by a CPU which executes a computer program. However, they may be implemented by a dedicated integrated circuit or circuits.

The display 300 will be described below. The display 300 comprises a display device such as a liquid crystal display device or a CRT. The display 300 displays a tomographic image of the blood vessel generated based on the received signal, and also displays the analyzed results produced by the time-series distortion value data analyzer 230. Specifically, the display 300 should preferably display the analyzed results superimposed on the tomographic image. For example, the display 300 may display a different hue added to the tomographic image depending on the analyzed results with respect to the location to be evaluated, i.e., the blood vessel wall or the plaque.

A processing sequence of the ultrasonic diagnostic system, i.e., sequence of the ultrasonic diagnostic method according to the present embodiment will be described below.

Figure 2:
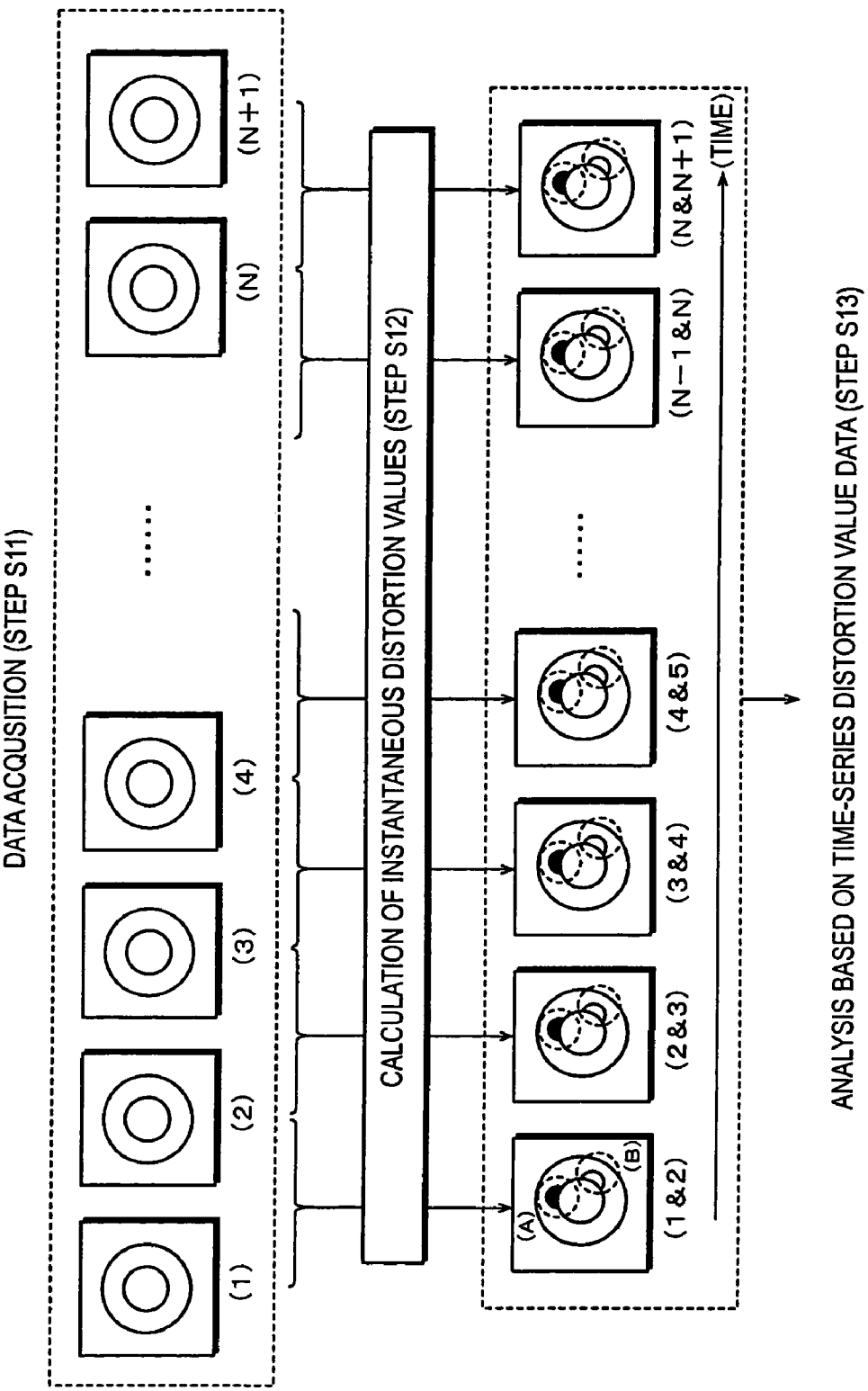
FIG. 2 is a diagram showing a concept of a processing sequence of the ultrasonic diagnostic system shown in FIG. 1.

FIG. 2 shows a concept of the processing sequence of the ultrasonic diagnostic system according to the present embodiment. As shown in FIG. 2, the processing sequence of the ultrasonic diagnostic system includes data acquisition (step S11), calculation of instantaneous distortion values (step S12), and analysis using time-series distortion value data (step S13) which are successively carried out.

In step S11, the data of a received signal (echo signal) at a plurality of times (first time through (N+1)th time) in a chronological sequence over a plurality of cardiac beats is acquired.

In step S12, the instantaneous distortion value calculator 220 acquires the data in step S11, and compares the data at kth and (k+1)th times (k represents an integer in the range from 1 to N), which are two chronologically adjacent times, with each other to calculate instantaneous distortion values at a plurality of times in a chronological sequence. In FIG. 2, the instantaneous distortion value calculator 220 calculates a total of N instantaneous distortion values.

In step S13, the time-series distortion value data analyzer 230 analyzes the state of a location to be evaluated, using the instantaneous distortion value data representing the instantaneous distortion values at the plurality of times which have been calculated in the chronological sequence in step S12. As a result, whether a lesion such as a plaque or the like exists in the location to be evaluated or not, and also the property and state of the plaque based on the dynamic characteristics of the plaque, are determined. Specifically, it is determined whether the plaque is a hard plaque or a soft plaque.

Figure 3:
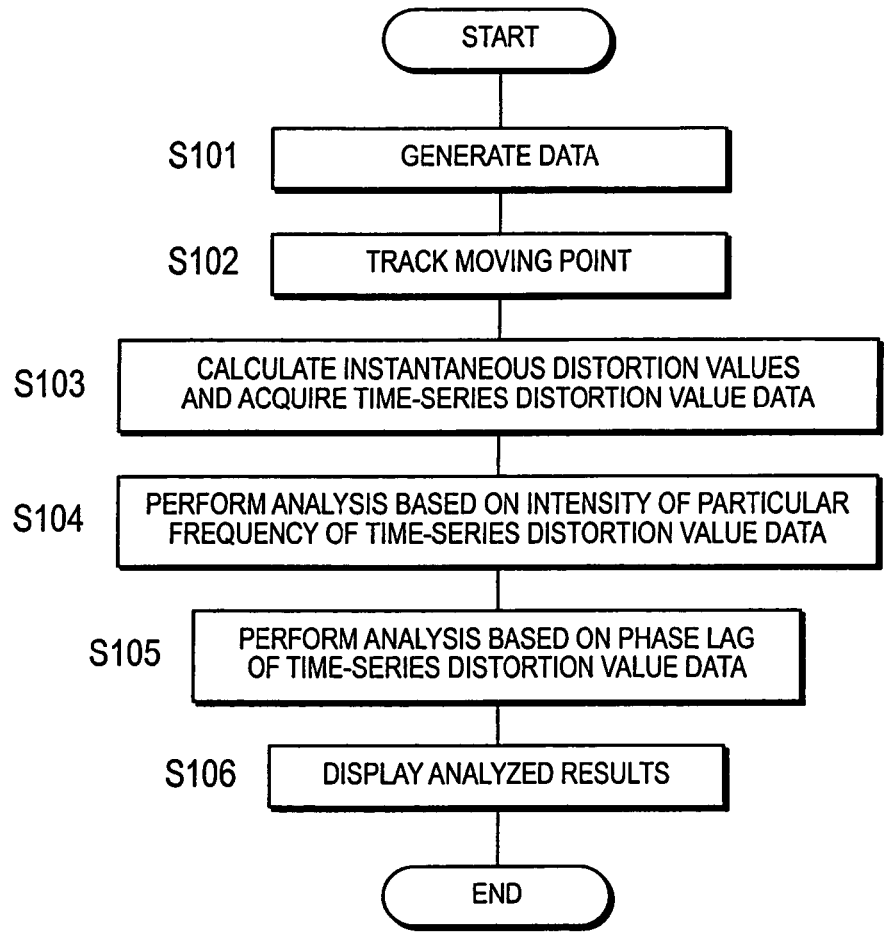
FIG. 3 is a flowchart of the processing sequence of the ultrasonic diagnostic system shown in FIG. 1.

FIG. 3 is a flowchart of the processing sequence of the ultrasonic diagnostic system according to the present embodiment. The processing sequence of the ultrasonic diagnostic system includes a data generating process, a moving point tracking process, a process of calculating instantaneous distortion values, an analyzing process based on the intensity of a particular frequency component of time-series distortion value data, an analyzing process based on a phase lag of the time-series distortion value data, and a process of displaying analyzed results. Details of these processes will be described below.

(Data Generating Process)

The data generating process is performed in step S101. Specifically, the data of received signals (echo signals) at a plurality of times in a chronological sequence over a plurality of cardiac beats are obtained. Specifically, an ultrasonic wave is applied in radial scanning to a blood vessel, and a reflected wave is received to generate tomographic image data (two-dimensional data) of the blood vessel at the plurality of times. In addition to the radial scanning, scanning along the longitudinal axis of the blood vessel may be performed for an expanded three-dimensional process. If such an expanded three-dimensional process is carried out, then three-dimensional volume data of the blood vessel are produced.

(Moving Point Tracking Process)

The movement of the point of a location to be evaluated in the lumen of the blood vessel is tracked in step S102. Specifically, since the blood vessel wall is distorted in response to cardiac beats, the point of the location to be evaluated is moved. In this step, the movement of the point of the location to be evaluated is tracked. Specifically, as shown in FIG. 2, the tracker 221 compares the data at kth and (k+1)th times, which are two chronologically adjacent times, with each other to track the moving point. For example, the moving point is tracked based on the data at the first time and the data at the second time.

The moving point tracking process employs an autocorrelation process or a composite autocorrelation process. Preferably, the composite autocorrelation process is employed. Details of the composite autocorrelation process will not be described below. Briefly, however, the composite autocorrelation process has a first stage in which signals that are successively acquired in response to cardiac beats are subjected to orthogonal detection. Then, using a complex envelope signal produced after the orthogonal detection, a position where the coefficient of correlation of envelope distributions before and after the deformation is highest is roughly estimated locally. In a second stage of the composite autocorrelation process, the position of the point is thoroughly checked from a phase difference at the estimated position where the correlation of the envelope distributions is highest.

Generally, when the ultrasonic catheter 100 is positionally shifted, ultrasonic scanning lines applied before and after the deformation cross each other, tending to cause an error in the detection of the phase difference. According to the composite autocorrelation process, prior to the detection of a phase difference, the position of the moving point is roughly estimated using a coefficient of correlation of envelope distributions which is less susceptible to the positional shift of the ultrasonic catheter 100, so that any adverse effect due to the error in the detection of the phase difference can be minimized. The coefficient of correlation of envelope distributions corresponds to a quantity representative of the degree of agreement between local waveforms before and after the deformation.

When the ultrasonic catheter 100 is inserted into a coronary artery, since it is directly affected by the movement of the heart, the relative position of the ultrasonic catheter 100 with respect to the blood vessel may be shifted along the longitudinal axis of the blood vessel during measurement over a long period of time. The composite autocorrelation process, however, can be expanded to a three-dimensional process comprising radial, circumferential, and longitudinal directions. If the ultrasonic diagnostic system 100 performs scanning along the longitudinal axis of the blood vessel in addition to radial scanning, then the composite autocorrelation process allows the ultrasonic diagnostic system 100 to track the moving point not only in the radial and circumferential direction, but also in the longitudinal direction.

According to the above moving point tracking process, a component $u_r^{(k)} = u_r^{(k)}(r,\theta,l;k\Delta t)$ in the radial direction r of a displacement between the kth and (k+1)th times, a component $u\theta^{(k)} = u\theta^{(k)}(r,\theta,l;k\Delta t)$ in the circumferential direction $\theta$ of the displacement, and a component $u_l^{(k)} = u_l^{(k)}(r,\theta,l;k\Delta t)$ in the longitudinal direction l of the displacement are determined. In the above equations, $\Delta t$ represents a sampling period, r, $\theta$, l represent coordinate values in the three-dimensional volume data at the kth time.

If a spatial point of the location to be evaluated which is to be noticed at the start of the processing sequence is represented by $p_0$ ($p_r^{(0)}=r_0$, $p\theta^{(0)}=\theta^{(0)}$, $P_l^{(0)}=l_0$), then the position to which this spatial point moves after the time $k\Delta t$ (i.e., kth time) is expressed by the following equations (1a) through (1c):

$$p_r^{(k)} = p_r^{(0)} + \sum_{i=0}^{k-1} u_r^{(i)}(p_r^{(i)}, p_\theta^{(i)}, p_l^{(i)}) \quad (1a)$$

$$p_\theta^{(k)} = p_\theta^{(0)} + \sum_{i=0}^{k-1} u_\theta^{(i)}(p_r^{(i)}, p_\theta^{(i)}, p_l^{(i)}) \quad (1b)$$

$$p_l^{(k)} = p_l^{(0)} + \sum_{i=0}^{k-1} u_l^{(i)}(p_r^{(i)}, p_\theta^{(i)}, p_l^{(i)}) \quad (1c)$$

After the moving point is tracked as described above, then control goes to the following process.

(Process of Calculating Instantaneous Distortion Values)

Then, instantaneous distortion values at a plurality of times in a chronological sequence are calculated in step S103. As a result, time-series distortion value data of instantaneous distortion values at a plurality of times in a chronological sequence are obtained.

Specifically, the instantaneous distortion value calculator 220 calculates a distortion value ε from a displacement, i.e., $(u_r^{(k)}, u\theta^{(k)}, u_l^{(k)})$, that is determined by the moving point tracking process between the data at the kth time and the data at the (k+1)th time, which are two chronologically adjacent times. More specifically, the distortion value ε is obtained by differentiating the components of the displacement with respect to r, θ, 1, respectively, according to the following equations (2a) through (2c):

$$\varepsilon_r^{(k)}(r, \theta, l) = \frac{\partial u_r^{(k)}(r, \theta, l)}{\partial r} \quad (2a)$$

$$\varepsilon_\theta^{(k)}(r, \theta, l) = \frac{\partial u_\theta^{(k)}(r, \theta, l)}{\partial \theta} \quad (2b)$$

$$\varepsilon_l^{(k)}(r, \theta, l) = \frac{\partial u_l^{(k)}(r, \theta, l)}{\partial l} \quad (2c)$$

Therefore, the distortion value after t=tΔk of the spatial point $(r_0, \theta_0, l_0)$ of the location to be evaluated which is to be noticed at the start of the processing sequence is calculated according to the equation (3) shown below, using the equations (1a) through (1c) and the equations (2a) through (2c). Though only a component in the radial direction of the distortion value is indicated, components in the circumferential and longitudinal direction can similarly be calculated.

$$\tilde{\varepsilon}_r(r_0, \theta_0, l_0; t) = \tilde{\varepsilon}_r(r_0, \theta_0, l_0; k\Delta t) \quad (3)$$
$$= \tilde{\varepsilon}_r(r_0, \theta_0, l_0)$$
$$= \varepsilon_r^{(k)}(p_r^{(k)}, p_\theta^{(k)}, p_l^{(k)})$$

According to the equation (3), instantaneous distortion values at a plurality of times t (tΔk) are calculated. As a result, time-series distortion value data of instantaneous distortion values at a plurality of times in a chronological sequence are obtained.

The time-series distortion value data represented by the equation (3) contain noise. Therefore, the instantaneous distortion value calculator 220 may further have a function to reduce the noise contained in the time-series distortion value data. For example, the instantaneous distortion value calculator 220 may reduce the noise contained in the time-series distortion value data according to a spatial local smoothing process, a bandpass filtering process, or a stabilizing process based on synchronous addition, which will be described below.

According to the spatial local smoothing process, ROI (regions of interest) which are local spatial regions are set up and a smoothing process is performed, as indicated by the equation (4) shown below. In the equation (4), a three-dimensional spatial ROI is represented by a symbol V.

$$\bar{\varepsilon}_r(r, \theta, l; t) = \frac{1}{V} \int_V \tilde{\varepsilon}_r(r', \theta', l'; t) dV \quad (4)$$

According to the bandpass filtering process, the bandpass filtering process which passes only certain frequencies is applied to the time-series distortion value data which has been subjected to the spatial local smoothing process indicated by the equation (4), according to the equation (5) shown below. Specifically, since the time-series distortion value data change periodically in response to cardiac beats, other components than the frequency components corresponding to the cardiac beats are highly likely to be noise. Therefore, by applying a bandpass filter set up across a frequency (1 Hz) corresponding to the cardiac beats to the time-series distortion value data, noise can be removed from the time-series distortion value data, thus extracting stable time-series distortion value data.

$$\hat{\varepsilon}_r(r, \theta, l; t) = BPF\{\bar{\varepsilon}_r(r, \theta, l; t)\} \quad (5)$$

Figure 4:
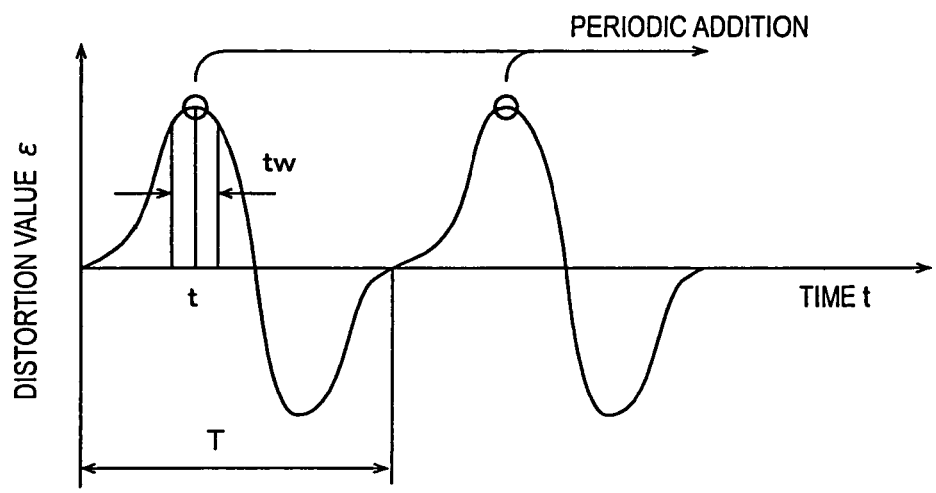
FIG. 4 is a diagram showing the principle of a stabilizing process based on synchronous addition, which is applicable in step S103 of the processing sequence shown in FIG. 3.

A stabilizing process based on synchronous addition may be carried out instead of the bandpass filtering process. According to the stabilizing process based on synchronous addition, based on the fact that the time-series distortion value data change periodically in response to cardiac beats, values in corresponding time regions are added over a plurality of periods, and averaged. FIG. 4 illustrates the principles of the stabilizing process based on synchronous addition.

As shown in FIG. 4, if the period of the time-series distortion value data is represented by T, then a region having a width tw with a time t at its center, and regions having respective widths tw with a time t+T, a time t+2T, a time t+3T, . . . , a time t+(N−1)T at their centers correspond to each other. The stabilizing process based on synchronous addition is a process for averaging the values of these corresponding regions. Stated otherwise, the stabilizing process based on synchronous addition is a chronological local averaging process according to the following equation (6):

$$\hat{\varepsilon}_r(r, \theta, l; t) = \frac{1}{N \cdot t_w} \sum_{i=0}^{N-1} \int_{-\frac{t_w}{2}}^{\frac{t_w}{2}} \bar{\varepsilon}_r(r, \theta, l; t + iT + t') dt' \quad (6)$$

As described above, in step S103 shown in FIG. 3, time-series distortion value data of distortion values at a plurality of times are calculated based on a change in the distance between two local points. According to the present embodiment, not only the spatial local smoothing process, but also the bandpass filtering process and the stabilizing process based on synchronous addition, are carried out to produce time-series distortion value data with reduced noise.

Figure 5:
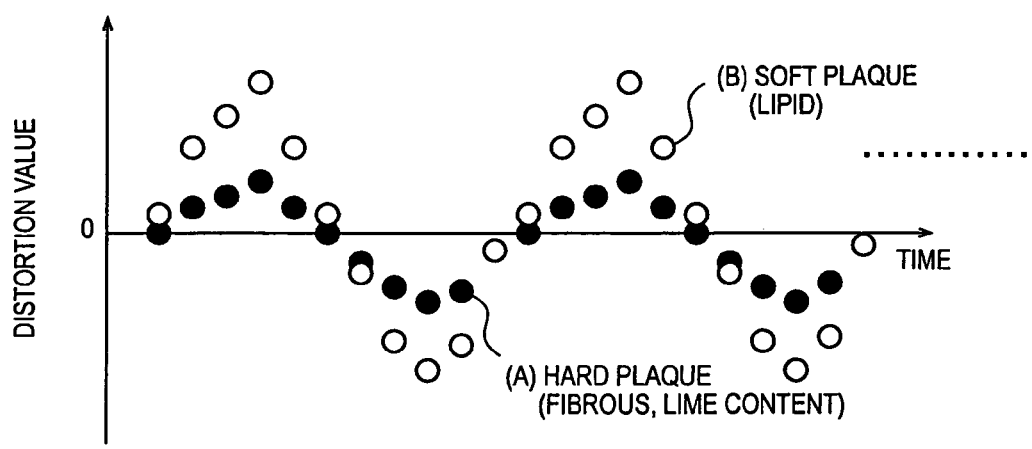
FIG. 5 is a diagram showing an example of time-series distortion data calculated in step S103 of the processing sequence shown in FIG. 3.

An example of the time-series distortion value data is shown in FIG. 5. FIG. 5 shows the time-series distortion value data which are obtained both when the location to be evaluated is a soft plaque with a high lipid content and when the location to be evaluated is a hard plaque with a high fibrous content, a high lime content, and a low lipid content.

Then, the state of the location to be evaluated, or preferably the state of the plaque, is analyzed based on the time-series distortion value data of instantaneous distortion values at a plurality of times which are calculated in a chronological sequence by the instantaneous distortion value calculator 220. The analysis includes an analysis based on the intensity of a particular frequency of the time-series distortion value data and an analysis based on a phase lag of the time-series distortion value data.

(Analysis Based on the Intensity of a Frequency)

In step S104 shown in FIG. 3, an analysis based on the intensity of a particular frequency of the time-series distortion value data is carried out. Specifically, the time-series distortion value data analyzer 230 divides the time-series distortion value data into a plurality of frequency components, and analyzes the state of the location to be evaluated based on the intensity of a particular one of the frequency components.

Specifically, a Fourier transform represented by the equation (7) shown below is applied to the time-series distortion value data determined at the spatial points (r, θ, l) of the location to be evaluated, thereby dividing the time-series distortion value data into a plurality of frequency components. Actually, the same process is performed on the time-series distortion value data determined at all the spatial points of the location to be evaluated.

$$E_r(r, \theta, l; \omega) = \int_{\infty}^{\infty} \hat{e}_r(r, \theta, l; t) e^{-j\omega t} dt \qquad (7)$$

Figure 6:
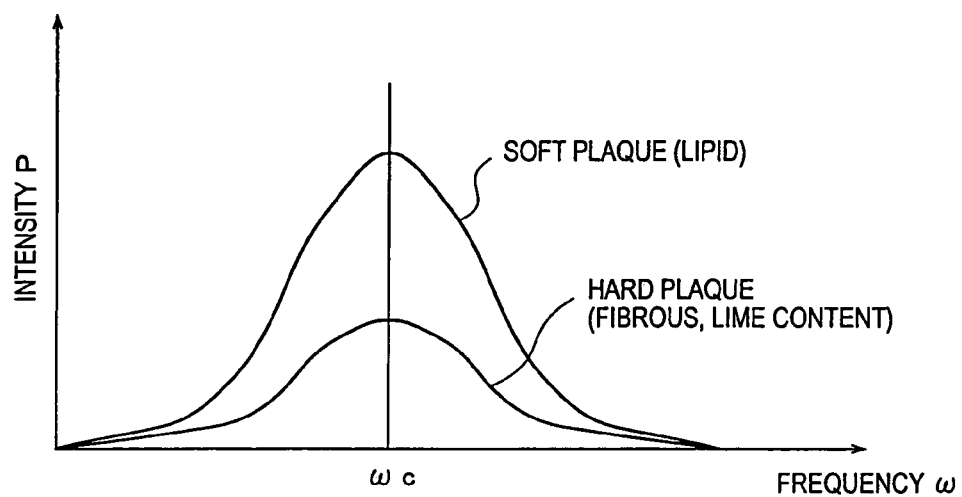
FIG. 6 is a diagram showing divided frequency components of the time-series distortion data analyzed in step S104 of the processing sequence shown in FIG. 3.

FIG. 6 shows the divided frequency components. In FIG. 6, the horizontal axis represents the frequency ω and the vertical axis the intensity P. The frequency ωc represents the frequency of cardiac beats, and is about 1 Hz. FIG. 6 shows the divided frequency components both when the location to be evaluated is a hard plaque and when the location to be evaluated is a soft plaque.

As shown in FIG. 6, the frequency intensity is maximum in the vicinity of the cardiac beat frequency of ωc irrespective of whether the location to be evaluated is a hard plaque or a soft plaque. The frequency intensity is higher when the location to be evaluated is a soft plaque than when the location to be evaluated is a hard plaque, and the difference between these frequency intensities is noticeable in the vicinity of the frequency of ωc.

Then, the time-series distortion value data analyzer 230 calculates the intensity of the frequency components in the vicinity of the cardiac beat frequency of ωc for each spatial point. As a result, it is possible to evaluate the property and state of the plaque irrespective of the stage of contraction and expansion of the blood vessel due to cardiac beats. Specifically, as indicated by the equation (8) shown below, the range of a width ωw with the cardiac beat frequency of ωc at its center is set up, and the frequency characteristics determined according to the equation (7) is integrated in the above range to calculate the intensity in the vicinity of the cardiac beat frequency of ωc. Specifically, the intensity in the vicinity of the cardiac beat frequency of ωc is calculated at a plurality of spatial points.

$$P_r(r, \theta, l) = \int_{\omega_c - \frac{\omega_w}{2}}^{\omega_c + \frac{\omega_w}{2}} |E_r(r, \theta, l; \omega)| d\omega \qquad (8)$$

It is preferable to regard a particular position (e.g., a position near the outer membrane of the blood vessel) as a reference point and standardize the intensity at each position based on the reference point. Using standardized values, it is possible to evaluate the hardness of the plaque stably in a semi-quantitative manner.

It is also possible to make an evaluation in view of a change in the time-series frequency intensity by dividing the time-series distortion value data calculated over an interval which is at least twice the period of cardiac beats into a plurality of frequency components using a Fourier transform, and evaluating the hardness of the plaque based on the frequency intensity in the vicinity of ωc.

Though the component in the radial direction r has been described above, components in the circumferential direction θ and the longitudinal direction l can also be evaluated by dividing the time-series distortion value data into a plurality of frequency components and using the frequency intensity in the vicinity of ωc.

A process of analyzing the state of the location to be evaluated, i.e., the state of the plaque, based on the phase lag of the time-series distortion value data will be described below.

(Analysis Based on Phase Lag of Time-Series Distortion Value Data)

According to the present embodiment, the analysis based on the intensity of a particular frequency of the time-series distortion value data (step S104 in FIG. 3) is followed by an analysis based on the phase lag of the time-series distortion value data (step S105). Specifically, the time-series distortion value data analyzer 230 compares the time-series distortion value data obtained at each spatial point and the time-series distortion value data obtained at a reference point (e.g., a position near the outer membrane of the blood vessel) with each other, calculates a phase lag between the time-series distortion value data, and analyzes the state of the location to be evaluated based on the magnitude of the phase lag.

More specifically, based on the fact that the time-series distortion value data determined at each spatial point (r, θ, l) of the location to be evaluated has ωc as the carrier angular frequency (cardiac angular frequency), orthogonal detection is performed on the time-series distortion value data using ωc as a reference frequency. As a result, as indicated by the equation (9) shown below, complex time-series distortion value data represented by an envelope portion vr and a portion relative to a phase φ is calculated.

$$\check{\epsilon}_r(r,\theta,l;t) = v_r(r,\theta,l;t) e^{j\phi(r,\theta,l;t)} \qquad (9)$$

where $v_r(r, \theta, l; t)$ represents an envelope portion and $\phi_r(r, \theta, l; t)$ represents a phase. Using the above equation (9), complex time-series distortion value data at any optional spatial point and complex time-series distortion value data at a reference point are calculated.

Then, a phase lag at any optional spatial point with respect to a reference point is determined based on the complex time-series distortion value data at the optional spatial point and the complex time-series distortion value data at the reference point.

Figure 7:
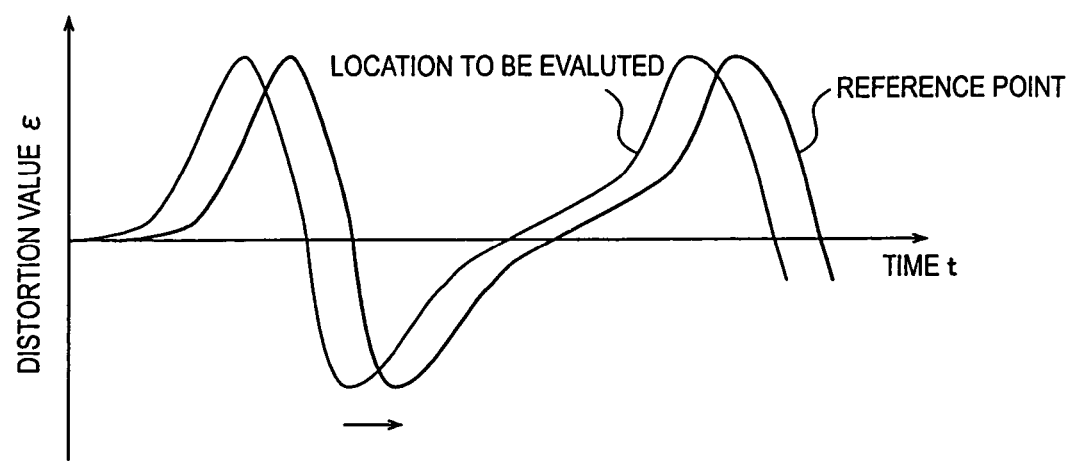
FIG. 7 is a diagram showing a phase lag of the time-series distortion data analyzed in step S105 of the processing sequence shown in FIG. 3.

FIG. 7 schematically shows a phase lag. Specifically, FIG. 7 shows time-series distortion value data at the reference point and time-series distortion value data at the location to be evaluated. In FIG. 7, the phase of the time-series distortion value data at the location to be evaluated lags behind the phase of time-series distortion value data at the reference point. The phase lag reflects viscoelasticity at the location to be evaluated. Specifically, if the plaque at the location to be evaluated is a soft plaque, then the phase lag is large, and if the plaque at the location to be evaluated is a hard plaque, then the phase lag is small. The reasons are that a hard plaque (stable plaque) which contains a lot of relatively hard fibrous components moves substantially in synchronism with the movement of the blood vessel wall depending on the cardiac beats, and a soft plaque (unstable plaque) which contains a lot of lipid components and a very small amount of fibrous components causes a response delay with respect to the movement of the blood vessel wall in a direction away from the interface with the blood vessel wall. Consequently, the property and state of the plaque can be analyzed by analyzing the phase lag. Specifically, a phase lag at any optional spatial point with respect to a reference point is determined by the following equation (10):

$$\Delta\phi_r(r;\theta,l) = arg\{\int_\infty^\infty \check{\epsilon}_r(r;\theta,l)\check{\epsilon}_{ro}^*(r_0,\theta_0, l_0;t)dt\} \quad (10)$$

That is, the product of a complex conjugate of the complex time-series distortion value data at the reference point and the complex time-series distortion value data at each spatial point of the location to be evaluated is determined and integrated with respect to time, and an argument of the result is produced to obtain a phase lag at any optional spatial point with respect to a reference point. In the equation (10), the time t is used as an integration variable, and the product is integrated with respect to time in order to taken stability into account and evaluate the property and state of the plaque without depending on the stages of contraction and expansion of the blood vessel due to cardiac beats.

Though the component in the radial direction r has been described above, a phase lag of the time-series distortion value data can also be determined with respect to components in the circumferential direction θ and the longitudinal direction l, and can similarly be evaluated.

As described above, the property and state of the location to be evaluated can be analyzed based on the intensity of a particular frequency of the time-series distortion value data (step S104) and/or the phase lag of the time-series distortion value data (step S105). (Display of analyzed results)

Then, the analyzed results are displayed on the display 300 (step S106 in FIG. 3). For example, a tomographic image along a plane perpendicular to the longitudinal axis of the blood vessel is displayed, and the analyzed results of step S104 and/or step S105 are displayed over the tomographic image.

Specifically, a hue is added to each position on the tomographic image based on the intensity of a particular frequency of the time-series distortion value data at each spatial point (step S104) and/or the phase lag of the time-series distortion value data (step S105). For example, a plurality of thresholds are set up, and the standard value of the intensity determined in step S104 is compared with those thresholds. Depending on the results of comparison with the thresholds, added hues can be changed. More specifically, a first hue can be applied to a region where the standard value of the intensity determined in step S104 is smaller than a first threshold, a second hue can be applied to a region where the standard value of the intensity is equal to or greater than the first threshold and smaller than a second threshold, and a third hue can be applied to a region where the standard value of the intensity is equal to or greater than the second threshold. Similarly, the value of the phase lag of the time-series distortion value data determined in step S105 can be compared with a plurality of thresholds, and added hues can be changed depending on the results of comparison with the thresholds.

According to the composite autocorrelation process used to track the moving point in step S102, a correlation coefficient is calculated simultaneously with a phase. The correlation coefficient exhibits a high value if the distortion value is small and the moving point is translated on the same plane.

A hard region (e.g., a hard plaque) has a tendency to make a motion close to a translation when deformed. Therefore, the value of the correlation coefficient of the hard region is higher than that of a soft region. Therefore, the value of the correlation coefficient itself serves to determine the property and state of the location to be evaluated. A distribution of correlation coefficients is advantageous in that it can stably be calculated. Therefore, when the display 300 displays the value of the correlation coefficient as well as the analyzed results, it can provide important information for the operator to determine the state of the location to be evaluated.

The value of the correlation coefficient is low in a region which moves fast. For example, a blood stream in the lumen of a blood vessel moves faster than the wall of the blood vessel. As a consequence, the blood stream in the lumen of the blood vessel has a lower correlation coefficient than the wall of the blood vessel.

Therefore, it can be determined whether the location to be evaluated is a blood stream or a blood vessel wall based on the different correlation coefficients. Specifically, a determined correlation coefficient is compared with a threshold, and a tomographic image of a region where the correlation coefficient is lower than the threshold is displayed with a reduced luminance on the display 300. As a result, the luminance of the blood stream is made lower in its entirety than the luminance of the blood vessel wall, so that the boundary between the blood stream and the blood vessel wall can clearly be displayed. Conversely, the luminance of a region where the correlation coefficient is higher may be increased. The boundary between the bloodstream and the blood vessel wall can thus be clarified by displaying the tomographic image with the luminance of a particular region of the tomographic image being changed based on the correlation coefficient.

The details of the ultrasonic diagnostic system according to the first embodiment has been described above. The ultrasonic diagnostic system according to the first embodiment can be modified in various ways. For example, in the above description, the analysis based on the intensity of a particular frequency of the time-series distortion value data (step S104) is followed by the analysis based on the phase lag of the time-series distortion value data (step S105). The order of these analytic steps may be changed. Furthermore, the state of the location to be evaluated may be analyzed by performing only one of the analysis based on the intensity of a frequency component (step S104) and the analysis based on the phase lag of the time-series distortion value data (step S105).

As described above, the ultrasonic diagnostic system according to the present embodiment analyzes the state of an object to be evaluated based on time-series distortion value data of instantaneous distortion values obtained at a plurality of times over a period of time which includes at least a plurality of cardiac beats. The time-series distortion value data reflect the nonlinearity and viscoelasticity of a blood vessel wall and a plaque at the location to be evaluated. Accordingly, the ultrasonic diagnostic system according to the present embodiment can analyze the state of the location to be evaluated in view of the nonlinearity and viscoelasticity of the blood vessel wall and the plaque.

According to the analysis based on the intensity of a frequency component (step S104), in particular, the hardness of a plaque can be evaluated stably semi-quantitative manner by an index independent of the stages of contraction and expansion of the blood vessel due to cardiac beats.

According to the analysis based on the phase lag of the time-series distortion value data (step S105), the property and state of a plaque can be interpreted based on a phase lag which is an index which strongly reflects the viscoelasticity of the location to be evaluated.

For calculating an instantaneous distortion value at each time, since a noise component is liable to be comprised, not only the spatial local smoothing process, but also the band-pass filtering process set up across a frequency corresponding to cardiac beats, and/or the stabilizing process based on synchronous addition, may be applied. Consequently, the noise component can be reduced and the spatial resolution is prevented from being lowered, while at the same time the chronological continuity of data can be maintained.

2nd Embodiment

According to the first embodiment described above, instantaneous distortion values are calculated, and the state of the location to be evaluated is analyzed based on time-series distortion value data of instantaneous distortion values at a plurality of times. A distortion value is an index relatively representing the hardness of the location to be evaluated, and does not directly indicates the hardness of the location to be evaluated. A modulus of elasticity (Young's modulus) E is used as an index indicating the hardness of the location to be evaluated.

According to the present embodiment, an instantaneous modulus of elasticity at a location to be evaluated in a blood vessel is calculated, and the state of the location to be evaluated is analyzed based on time-series modulus-of-elasticity data of instantaneous modulus-of-elasticity values calculated at a plurality of times in a chronological sequence. Those parts of the ultrasonic diagnostic apparatus according to the second embodiment which are identical to those of the ultrasonic diagnostic apparatus according to the first embodiment are denoted by identical reference numerals.

Figure 8:
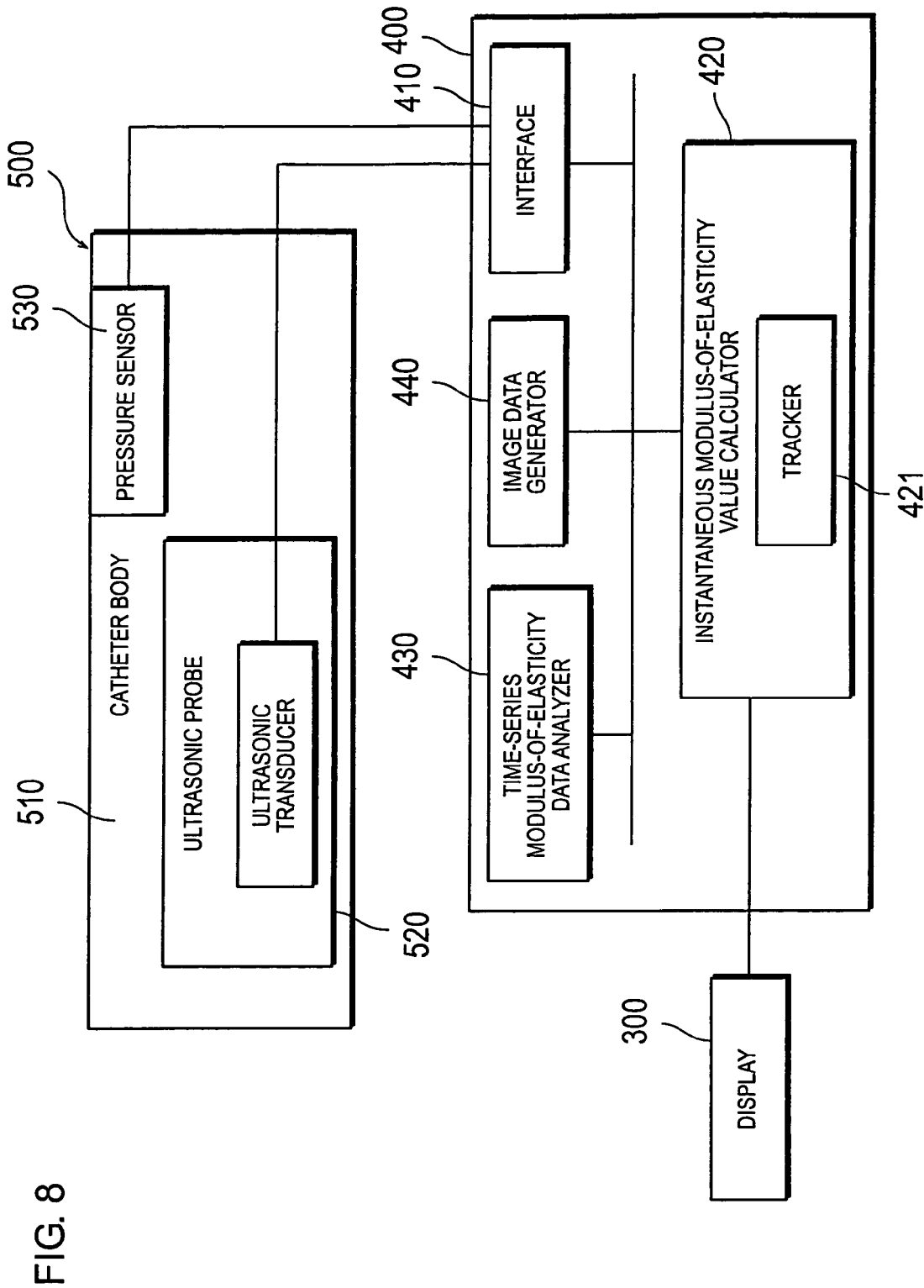
FIG. 8 is a block diagram of an ultrasonic diagnostic system according to a second embodiment of the present invention.

FIG. 8 shows in block form an ultrasonic diagnostic system according to the present embodiment. Of the ultrasonic diagnostic system according to the present embodiment, a display 300 is identical to the display of the according to the first embodiment. Therefore, the display 300 will not be described in detail below.

An ultrasonic catheter 500 according to the present embodiment has a catheter body 510 and a pressure sensor 530 mounted on the surface of the catheter body 510. The pressure sensor 530 is disposed at a proximal end of an area where an ultrasonic probe 520 exists and most closely to the ultrasonic probe 520, for measuring the pressure of the blood (blood pressure) in a blood vessel.

A controller 400 according to the present embodiment has an interface 410, an instantaneous modulus-of-elasticity value calculator 420, a time-series modulus-of-elasticity data analyzer 430, and an image data generator 440. The image data generator 440 has the same function as the image data generator 240 according to the first embodiment.

The interface 410 captures a received ultrasonic signal obtained by the ultrasonic probe 520 of the ultrasonic catheter 500 in the same manner as the interface 210 according to the first embodiment, and also captures a signal representing the blood pressure obtained by the pressure sensor 530.

The instantaneous modulus-of-elasticity value calculator 420 calculates instantaneous moduli of elasticity at the location to be evaluated in the blood vessel. Specifically, the instantaneous modulus-of-elasticity calculator 420 calculates an instantaneous modulus of elasticity at each point of time when the blood vessel is contracted and expanded by cardiac beats. The instantaneous modulus-of-elasticity calculator 420 calculates an instantaneous modulus of elasticity in each sampling period which is shorter than the period of cardiac beats, and performs such calculations over a plurality of cardiac beats. In this manner, the instantaneous modulus-of-elasticity calculator 420 produces time-series data of instantaneous moduli of elasticity (hereinafter referred to as "time-series modulus-of-elasticity data") at a plurality of times which are calculated in a chronological sequence. The instantaneous modulus-of-elasticity calculator 420 has a tracker 421 for tracking the position of the location to be evaluated in the blood vessel. The tracker 421 tracks the position of the location to be evaluated in the blood vessel according to an autocorrelation process or a composite autocorrelation process, as with the tracker 221 according to the first embodiment.

Generally, the relationship of a modulus of elasticity E, a distortion value $\epsilon$, and a stress $\sigma$ is given by the equation (11) shown below. While the variables are represented as Scalar quantities, the equation can be expanded to cover vector quantities.

$$\sigma = E \cdot \epsilon \quad (11)$$

Therefore, an instantaneous modulus of elasticity can be determined by calculating an instantaneous distortion value and a stress. The instantaneous modulus-of-elasticity calculator 420 has a function to calculate an instantaneous distortion value in the same manner as with the instantaneous distortion value calculator 220 according to the first embodiment, and also has a function to calculate a stress. The instantaneous modulus-of-elasticity calculator 420 calculates an instantaneous modulus of elasticity from the instantaneous distortion value and the stress.

The time-series modulus-of-elasticity data analyzer 430 analyzes the state of the location to be evaluated based on the time-series modulus-of-elasticity data obtained by the instantaneous modulus-of-elasticity calculator 420. The time-series modulus-of-elasticity data analyzer 430 determines whether the plaque in the location to be evaluated is a soft plaque or a hard plaque based on the dynamic nature of the plaque. Stated otherwise, the time-series modulus-of-elasticity data analyzer 430 evaluates the proportion of a lipid component of the plaque based on the dynamic nature of the plaque.

That the state of the location to be evaluated is analyzed based on the time-series modulus-of-elasticity data which includes information about the dynamic nonlinearity and viscoelasticity of the location to be evaluated, such as a blood vessel wall or a plaque, constitutes a feature of the ultrasonic diagnostic system according to the present embodiment. The time-series modulus-of-elasticity data analyzer 430 should preferably have a first function to divide the time-series modulus-of-elasticity data into a plurality of frequency components and analyze the state of the location to be evaluated based on the intensity of a certain one of the frequency components, and a second function to analyze the state of the location to be evaluated based on a phase lag (which may be a phase lead) of the time-series modulus-of-elasticity data. However, the time-series modulus-of-elasticity data analyzer 430 may have either the first function or the second function. The time-series modulus-of-elasticity data analyzer 430 can also calculate a rate of time-dependent change of the modulus of elasticity to analyze the location to be evaluated.

A processing sequence of the ultrasonic diagnostic system, i.e., sequence of the ultrasonic diagnostic method according to the present embodiment will be described below.

Figure 9:
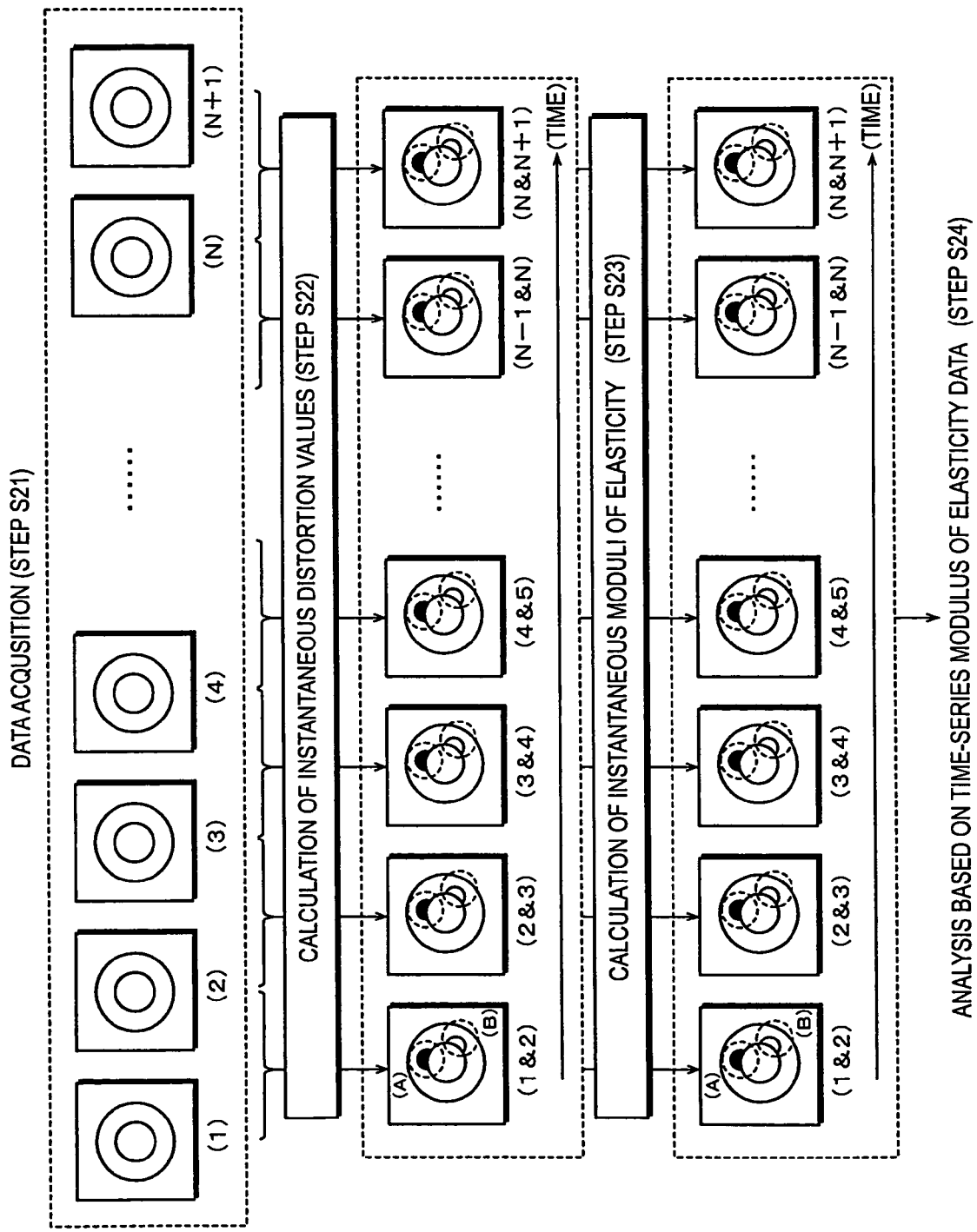
FIG. 9 is a diagram showing a processing sequence of the ultrasonic diagnostic system shown in FIG. 8.

FIG. 9 shows a concept of the processing sequence of the ultrasonic diagnostic system according to the present embodiment. As shown in FIG. 9, the processing sequence of the ultrasonic diagnostic system includes data acquisition (step S21), calculation of instantaneous distortion values (step S22), calculation of instantaneous moduli of elasticity (step S23), and analysis using time-series modulus-of-elasticity data (step S24) which are successively carried out. The data acquisition (step S21) and the calculation of instantaneous distortion values (step S22) are the same as those in step S11 and step S12 according to the first embodiment shown in FIG. 2.

In step S23, a stress in the blood vessel is calculated, and an instantaneous modulus of elasticity is calculated from the stress and the instantaneous distortion value determined in step S12.

In step S24, an analysis is made using time-series modulus-of-elasticity data. The analysis in step S24 is the same as the analysis in step S13 except that the time-series data used for the analysis is not time-series distortion value data, but time-series modulus-of-elasticity data.

Figure 10:
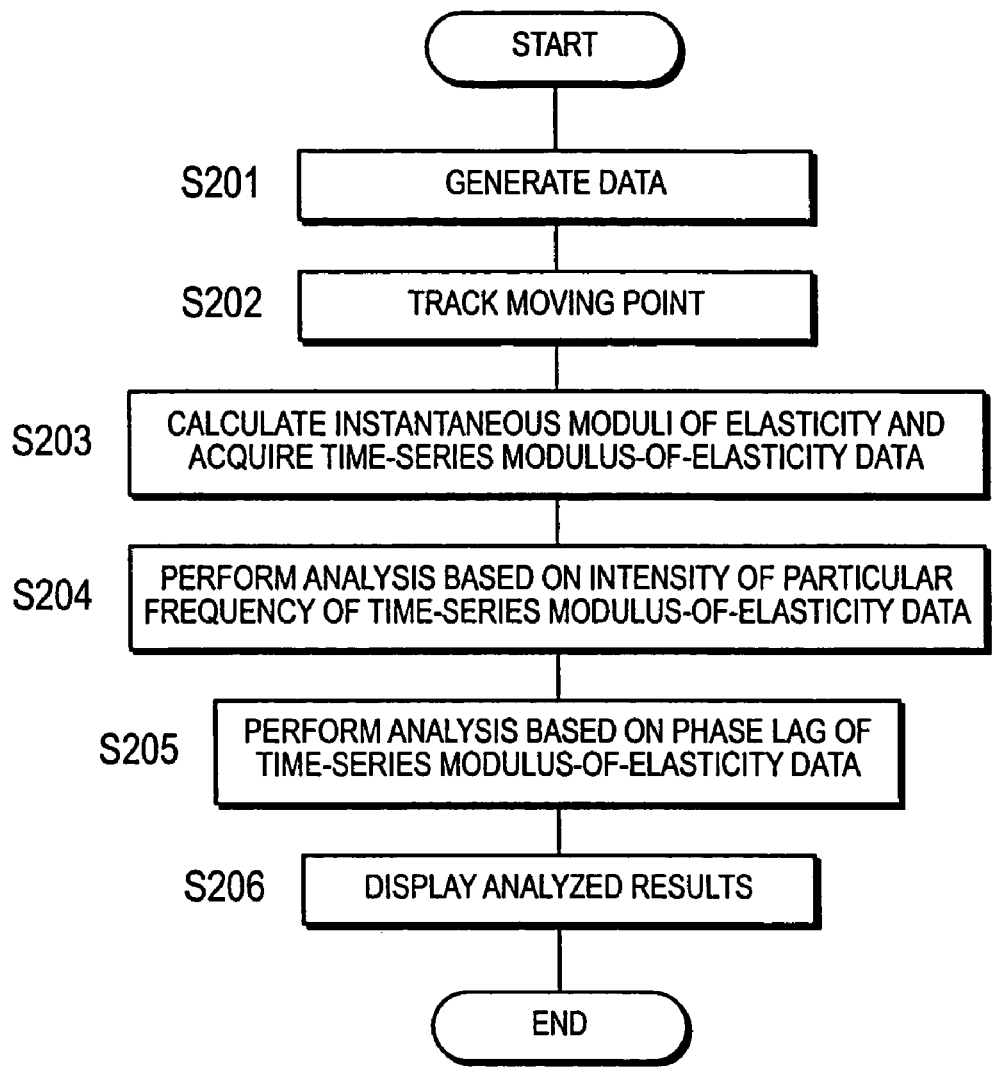
FIG. 10 is a flowchart of the processing sequence of the ultrasonic diagnostic system shown in FIG. 8.

FIG. 10 is a flowchart of the processing sequence of the ultrasonic diagnostic system according to the present embodiment. The processing sequence of the ultrasonic diagnostic system includes a data generating process, a moving point tracking process, a process of calculating instantaneous moduli of elasticity, an analyzing process based on the intensity of a particular frequency component of time-series modulus-of-elasticity data, an analyzing process based on a phase lag of time-series distortion value data, and a process of displaying analyzed results. The data generating process (step S201) and the moving point tracking process (step S202) are the same as those according to the first embodiment, and will not be described in detail below. (Process of calculating instantaneous moduli of elasticity)

Instantaneous moduli of elasticity at a plurality of times in a chronological sequence are calculated in step S203. As a result, time-series modulus-of-elasticity data of instantaneous moduli of elasticity at a plurality of times in a chronological sequence are obtained.

Specifically, the instantaneous modulus-of-elasticity calculator 420 determines instantaneous moduli of elasticity at a plurality of times. Instantaneous distortion values at a plurality of times can be calculated in the same manner as with the first embodiment, and hence the process of calculating such instantaneous distortion values will not be described below. The instantaneous modulus-of-elasticity calculator 420 also estimate stresses at the location to be evaluated in the blood vessel at the respective times. Then, the instantaneous modulus-of-elasticity calculator 420 calculates instantaneous moduli of elasticity at a plurality of times based on the instantaneous distortion values at the location to be evaluated and the estimated stresses at the respective times.

As tress at the location to be evaluated in the blood vessel wall is calculated according to a finite element method described below, for example.

A change in the blood pressure in the lumen of the blood vessel is measured by the pressure sensor 530 at the same time that an ultrasonic diagnosis is made using the ultrasonic catheter 500.

Based on the data obtained in step S201, a region of the blood vessel wall is extracted. The extracted region is divided into a mesh and modeled. Using the blood pressure change in the lumen of the blood vessel, a finite element analysis is performed to calculate a stress in each element of the mesh. The calculated stress is regarded as a local stress in the blood vessel wall. Finally, an instantaneous modulus of elasticity is calculated using the calculated stress according to the above equation (11).

In step S203 shown in FIG. 10, as described above, time-series modulus-of-elasticity data of moduli of elasticity at a plurality of times are calculated based on a change in the distance between two local points.

Then, based on the time-series modulus-of-elasticity data of moduli of elasticity that are calculated at a plurality of times in a chronological sequence by the instantaneous modulus-of-elasticity calculator 420, the state of the location to be evaluated or preferably the state of the plaque is analyzed. The analysis includes an analysis based on the intensity of a particular frequency of the time-series modulus-of-elasticity data and an analysis based on a phase lag of the time-series modulus-of-elasticity data.

After step S203, the state of the location to be evaluated or preferably the state of the plaque is analyzed based on the time-series modulus-of-elasticity data of moduli of elasticity that are calculated at a plurality of times in a chronological sequence by the instantaneous modulus-of-elasticity calculator 420. The includes an analysis based on the intensity of a particular frequency of the time-series modulus-of-elasticity data and an analysis based on a phase lag of the time-series modulus-of-elasticity data.

(Analysis Based on the Intensity of a Frequency)

An analysis based on the intensity of a particular frequency of the time-series modulus-of-elasticity data is carried out (step S204). Specifically, the time-series modulus-of-elasticity data analyzer 430 divides the time-series modulus-of-elasticity data into a plurality of frequency components, and analyzes the state of the location to be evaluated based on the intensity of a particular one of the frequency components. For example, the time-series modulus-of-elasticity data analyzer 430 calculates a frequency intensity in the vicinity of the frequency $\omega c$ of cardiac beats. The stronger the frequency intensity and the greater the modulus of elasticity, the harder the location to be evaluated. That is, a soft plaque has a smaller modulus of elasticity than a hard plaque. The processing in step S204 is the same as the processing in step S104 shown in FIG. 3 except that the time-series data to be processed are time-series modulus-of-elasticity data. Therefore, the processing in step S204 will not be described in detail below.

(Analysis Based on Phase Lag of Time-Series Modulus-of-Elasticity Data)

An analysis based on the phase lag of time-series modulus-of-elasticity data will be described below.

According to the present embodiment, the analysis based on the intensity of a particular frequency of the time-series modulus-of-elasticity data (step S204) is followed by an analysis based on the phase lag of the time-series modulus-of-elasticity data (step S205). Specifically, the time-series modulus-of-elasticity data analyzer 430 compares the time-series modulus-of-elasticity data obtained at each spatial point and the time-series modulus-of-elasticity data obtained at a reference point (e.g., a position near the outer membrane of the blood vessel) with each other, calculates a phase lag between the time-series modulus-of-elasticity data, and analyzes the state of the location to be evaluated based on the magnitude of the phase lag. In this case, too, if the plaque at the location to be evaluated is a soft plaque, then the phase lag is large, and if the plaque at the location to be evaluated is a hard plaque, then the phase lag is small. Consequently, the property and state of the plaque can be analyzed by analyzing the phase lag. The processing in step S205 is the same as the processing in step S105 shown in FIG. 3 except that the time-series data to be processed are time-series modulus-of-elasticity data. Therefore, the processing in step S205 will not be described in detail below.

(Display of Analyzed Results)

Then, the analyzed results are displayed on the display 300 (step S206). The processing in step S206 is the same as the processing in step S106 except that the analyzed results produced by the time-series modulus-of-elasticity data analyzer 430 (step S204 and/or step S205), rather than the analyzed results produced by the time-series distortion value data analyzer 230 (step S104 and/or step S105), are displayed over the tomographic image. Therefore, the processing in step S206 will not be described in detail below.

In the above description, the instantaneous modulus-of-elasticity calculator 420 calculates the value of an absolute modulus of elasticity based on the value of the blood pressure in the lumen of the blood vessel. The present embodiment, however, is not limited to such a process. Rather, the instantaneous modulus-of-elasticity calculator 420 may calculate a relative modulus of elasticity using a given reference position in the blood vessel as a point of reference (i.e., a modulus of elasticity at the time the distortion value in the entire blood vessel wall is normalized by the distortion value in a certain region).

In the above description, the pressure sensor 530 mounted on the ultrasonic catheter 500 is used to obtain the value of the blood pressure in the lumen of the blood vessel. However, the value of an absolute modulus of elasticity may be calculated by connecting an ordinary electronic tonometer having an arm band to the interface 410. It is preferable to use the pressure sensor 530 mounted on the ultrasonic catheter 500 as it can obtain a blood pressure at the same location as the region which is ultrasonically diagnosed.

If a calcified area is present on the surface of the lumen of the blood vessel, then a region of the blood vessel wall cannot be extracted because of a shortage of sufficient echo strength behind the calcified area. For this reason, an absolute modulus of elasticity may be calculated for a blood vessel where a region of the blood vessel wall can be extracted, and a relative modulus of elasticity may be calculated for a blood vessel where a region of the blood vessel wall cannot be extracted. In this case, though a relative modulus of elasticity is involved, the elasticity of the entire blood vessel wall can be evaluated under the same conditions.

In the above embodiment, the analysis based on the intensity of a particular frequency (step S204) is followed by the analysis based on the phase lag of the time-series modulus-of-elasticity data (step S205). The order of these analytic steps may be changed. Furthermore, the state of the location to be evaluated may be analyzed by performing only one of the analysis based on the intensity of a frequency component (step S204) and the analysis based on the phase lag of the time-series modulus-of-elasticity data (step S205).

As described above, the ultrasonic diagnostic system according to the present embodiment analyzes the state of an object to be evaluated based on time-series modulus-of-elasticity data of instantaneous moduli of elasticity obtained at a plurality of times over a period of time which includes at least a plurality of cardiac beats. The time-series modulus-of-elasticity data reflect the nonlinearity and viscoelasticity of a blood vessel wall and a plaque at the location to be evaluated. Accordingly, the ultrasonic diagnostic system according to the present embodiment can analyze the location to be evaluated in view of the nonlinearity and viscoelasticity of the blood vessel wall and the plaque.

The referred embodiments of the present invention have been described above. However, the present invention should not be limited by those embodiments, but maybe modified in various ways within the scope of the technical concept of the invention.

For example, the analysis based on the time-series distortion value data described in the first embodiment and the analysis based on the time-series modulus-of-elasticity data described in the second embodiment may be carried out by a single ultrasonic diagnostic system.

The present invention is applicable to any system for analyzing the state of a location to be evaluated based on time-series data of instantaneous distortion values or instantaneous moduli of elasticity (time-series distortion value data or time-series modulus-of-elasticity data) calculated at a plurality of times in a chronological sequence, and may employ a data processing process different from the data processing process described in the above embodiments. For example, the state of the location to be evaluated may be analyzed not based on frequency characteristics or phase characteristics, but by calculating a time-dependent rate of increase or decrease of moduli of elasticity in the time-series modulus-of-elasticity data in a time domain or a time-dependent rate of increase or decrease of distortions in the time-series distortion value data. For example, the state of the location to be evaluated may be analyzed directly from a rate of increase or decrease in the time-series data shown in FIG. 5. In this case, since the state of the location to be evaluated is analyzed based on the time-series data which includes information about the dynamic nonlinearity and viscoelasticity of the location to be evaluated, such as a blood vessel wall or a plaque, the state of the location to be evaluated can be analyzed highly accurately in view of the effects of the dynamic nonlinearity and viscoelasticity.

According to the present invention, as described above, inasmuch as the state of a location to be evaluated is analyzed based on time-series data of instantaneous distortion values or instantaneous moduli of elasticity calculated at a plurality of times in a chronological sequence, and the analyzed results are displayed, it is possible to determine the state of the location to be evaluated in view of the effects of the dynamic nonlinearity and viscoelasticity of a blood vessel and a plaque at the location to be evaluated. Consequently, the property and state of the blood vessel wall can be analyzed more intuitively and accurately, allowing operators to make a more objective diagnosis without significant differences. As a result, the operators can select a uniform, appropriate therapeutic process.

In particular, because the instantaneous distortion values or instantaneous moduli of elasticity are calculated at a plurality of times during a period of plural cardiac beats, it is possible to determine the state of the location to be evaluated in view of all the states comprising the stages of contraction and expansion of the blood vessel. The stabilizing process based on synchronous addition, referred to above, can be applied by calculating the instantaneous distortion values or instantaneous moduli of elasticity at a plurality of times during a period of plural cardiac beats. Consequently, the noise component can be reduced and the spatial resolution is prevented from being lowered, while at the same time the chronological continuity of data can be maintained.

In particular, since the time-series distortion value data are divided into a plurality of frequency components and the state of the location to be evaluated is analyzed based on the intensity of a certain one of the frequency components, different properties and states of plaques can be distinguished with high sensitivity in view of the effects of the dynamic nonlinearity and viscoelasticity of the plaques and blood vessel walls by selecting certain frequencies which allow the differences between the properties and states of the plaques and the blood vessel walls to be easily recognizable.

Because the state of the location to be evaluated is analyzed based on the phase lag of the time-series data, the properties and states of plaques and blood vessel walls can be analyzed in view of the differences therebetween.

Furthermore, a tomographic image is displayed with a change in the luminance of a region where a correlation coefficient obtained by the autocorrelation process or the composite autocorrelation process is low. Consequently, the analyzed results of the state of the location to be evaluated can be displayed with a clear boundary shown between a blood stream and a blood vessel wall.

An ultrasonic wave is transmitted while scanning the blood vessel in its circumferential direction and is also transmitted while scanning the blood vessel in its longitudinal direction, making it possible to track the position of the location to be evaluated which moves in the longitudinal direction of the blood vessel. Therefore, the processing means of the present invention is also applicable even if the relative position between the ultrasonic wave transmitting means and the blood vessel tends to be shifted in the longitudinal direction of the blood vessel. The ultrasonic diagnostic apparatus according to the present invention can acquire not only tomographic image data but also three-dimensional volume data, and can be expanded in processing to an analysis of pulse waves.

Although certain preferred embodiments of the present invention have been shown and described in detail, it should be understood that various changes and modifications may be made therein without departing from the scope of the appended claims.

What is claimed is:

1. An ultrasonic diagnostic apparatus comprising:
an insert to be inserted into a blood vessel;
an ultrasonic transducer mounted on said insert for transmitting an ultrasonic wave in the blood vessel, receiving a reflection of the ultrasonic wave, and producing a received signal representative of the received reflection;
a distortion value calculator which calculates an instantaneous distortion value at a location to be evaluated in the blood vessel based on said received signal;
an analyzer which analyzes a state of the location to be evaluated using time-series data of instantaneous distortion values which are calculated at a plurality of times in a chronological sequence by said distortion value calculator; and
a display which displays an analyzed result produced by said analyzer;
wherein said ultrasonic transducer moves along the longitudinal direction of the blood vessel to scan the blood vessel in the longitudinal direction of the blood vessel, while also scanning the blood vessel in a circumferential direction of the blood vessel; and
wherein said distortion value calculator tracks the position of the location to be evaluated along the longitudinal direction of the blood vessel.

2. An ultrasonic diagnostic apparatus according to claim 1, wherein said analyzer divides said time-series data into a plurality of frequency components and analyzes the state of the location to be evaluated based on the intensity of a particular one of the frequency components.

3. An ultrasonic diagnostic apparatus according to claim 2, wherein said analyzer judges that the proportion of a lipid component of a plaque formed in said blood vessel is higher as said intensity is higher.

4. An ultrasonic diagnostic apparatus according to claim 1, wherein said analyzer analyzes the state of the location to be evaluated based on a phase lag of said time-series data.

5. An ultrasonic diagnostic apparatus according to claim 4, wherein said analyzer judges that the proportion of a lipid component of a plaque formed in said blood vessel is higher as said phase lag is greater.

6. An ultrasonic diagnostic apparatus according to claim 1, wherein said distortion value calculator tracks the position of the location to be evaluated in the blood vessel according to an autocorrelation process or a composite autocorrelation process.

7. An ultrasonic diagnostic apparatus according to claim 1, wherein said display displays a tomographic image of the blood vessel based on said received signal and displays the analyzed result produced by said analyzer over said tomographic image.

8. An ultrasonic diagnostic apparatus according to claim 7, said distortion value calculator tracks the position of the location to be evaluated in the blood vessel according to an autocorrelation process or a composite autocorrelation process.

9. An ultrasonic diagnostic apparatus according to claim 8, said display displays said tomographic image with a change in the luminance of a particular region of said tomographic image based on a correlation coefficient obtained based on said autocorrelation process or said composite autocorrelation process.

10. An ultrasonic diagnostic apparatus according to claim 1, wherein said distortion value calculator reduces noise comprised in said time-series data.

11. An ultrasonic diagnostic apparatus comprising:
an insert to be inserted into a blood vessel;
an ultrasonic transducer mounted on said insert for transmitting an ultrasonic wave in the blood vessel, receiving a reflection of the ultrasonic wave, and producing a received signal representative of the received reflection;
a modulus-of-elasticity calculator which calculates an instantaneous modulus of elasticity at a location to be evaluated in the blood vessel based on said received signal;
an analyzer which analyzes a state of the location to be evaluated using time-series data of instantaneous moduli of elasticity which are calculated at a plurality of times in a chronological sequence by said modulus-of-elasticity calculator; and
a display which displays an analyzed result produced by said analyzer.

12. An ultrasonic diagnostic apparatus according to claim 11, wherein said analyzer divides said time-series data into a plurality of frequency components and analyzes the state of the location to be evaluated based on the intensity of a particular one of the frequency components.

13. An ultrasonic diagnostic apparatus according to claim 12, wherein said analyzer judges that the proportion of a lipid component of a plaque formed in said blood vessel is lower as said intensity is higher.

14. An ultrasonic diagnostic apparatus according to claim 11, wherein said analyzer analyzes the state of the location to be evaluated based on a phase lag of said time-series data.

15. An ultrasonic diagnostic apparatus according to claim 14, wherein said analyzer judges that the proportion of a lipid component of a plaque formed in said blood vessel is higher as said phase lag is greater.

16. An ultrasonic diagnostic apparatus according to claim 11, wherein said modulus-of-elasticity calculator tracks the position of the location to be evaluated in the blood vessel according to an autocorrelation process or a composite autocorrelation process.

17. An ultrasonic diagnostic apparatus according to claim 16, wherein said ultrasonic transducer transmits the ultrasonic wave while scanning the blood vessel in a circumferential direction thereof and transmits the ultrasonic wave while scanning the blood vessel in a longitudinal direction thereof.

18. An ultrasonic diagnostic apparatus according to claim 17, said modulus-of-elasticity calculator can track the position of the location to be evaluated which moves in the longitudinal direction of the blood vessel.

19. An ultrasonic diagnostic apparatus according to claim 11, wherein said display displays a tomographic image of the blood vessel based on said received signal and displays the analyzed result produced by said analyzer over said tomographic image.

20. An ultrasonic diagnostic apparatus according to claim 19, said modulus-of-elasticity calculator tracks the position of the location to be evaluated in the blood vessel according to an autocorrelation process or a composite autocorrelation process.

21. An ultrasonic diagnostic apparatus according to claim 20, said display displays said tomographic image with a change in the luminance of a particular region of said tomographic image based on a correlation coefficient obtained based on said autocorrelation process or said composite autocorrelation process.

22. An ultrasonic diagnostic apparatus according to claims 21, wherein said modulus-of-elasticity calculator reduces noise comprised in said time-series data.

23. An ultrasonic diagnostic apparatus according to claim 11, wherein said modulus-of-elasticity calculator calculates an absolute modulus of elasticity based on a blood pressure.

24. An ultrasonic diagnostic apparatus according to claim 11, wherein said modulus-of-elasticity calculator calculates a relative modulus of elasticity using a given reference point in said blood vessel as a point of reference.

25. An ultrasonic diagnostic apparatus according to claim 11, wherein said ultrasonic transducer moves along the longitudinal direction of the blood vessel to scan the blood vessel in the longitudinal direction of the blood vessel, while also scanning the blood vessel in a circumferential direction thereof, and wherein said modulus-of-elasticity calculator can track the position of the location to be evaluated as it moves in the longitudinal direction of the blood vessel.

26. An ultrasonic diagnostic method comprising steps of:
   (1) transmitting an ultrasonic wave in a blood vessel, receiving a reflection of the ultrasonic wave, and producing a received signal representative of the received reflection;
   (2) calculating an instantaneous distortion value at a location to be evaluated in the blood vessel based on said received signal;
   (3) analyzing a state of the location to be evaluated using time-series data of instantaneous distortion values which are calculated at a plurality of times in a chronological sequence; and
   (4) displaying an analyzed result produced in said step (3).

27. An ultrasonic diagnostic method according to claim 26, wherein said step (3) comprises the step of dividing said time-series data into a plurality of frequency components and analyzing the state of the location to be evaluated based on the intensity of a particular one of the frequency components.

28. An ultrasonic diagnostic method according to claim 27, wherein said step (3) comprises the step of judging that the proportion of a lipid component of a plaque toned in said blood vessel is higher as said intensity is higher.

29. An ultrasonic diagnostic method according to claim 26, wherein said step (3) comprises the step of analyzing the state of the location to be evaluated based on a phase lag of said time-series data.

30. An ultrasonic diagnostic method according to claim 29, wherein said step (3) comprises the step of judging that the proportion of a lipid component of a plaque formed in said blood vessel is higher as said phase lag is greater.

31. An ultrasonic diagnostic method according to claim 26, wherein said step (2) comprises the step of tracking the position of the location to be evaluated in the blood vessel according to an autocorrelation process or a composite autocorrelation process.

32. An ultrasonic diagnostic method according to claim 31, wherein said step (1) comprises the step of transmitting the ultrasonic wave while scanning the blood vessel in a circumferential direction thereof, and transmitting the ultrasonic wave while scanning the blood vessel in a longitudinal direction thereof.

33. An ultrasonic diagnostic method according to claim 32, wherein said tracking step allows tracking of the position of the location to be evaluated which moves in the longitudinal direction of the blood vessel.

34. An ultrasonic diagnostic method according to claim 26, wherein said step (4) comprises the step of displaying a tomographic image of the blood vessel based on said received signal and displaying the analyzed result over said tomographic image.

35. An ultrasonic diagnostic method according to claim 34, wherein said step (2) comprises the step of tracking the position of the location to be evaluated in the blood vessel according to an autocorrelation process or a composite autocorrelation process.

36. An ultrasonic diagnostic method according to claim 35, wherein said step (4) comprises the step of displaying said tomographic image with a change in the luminance of a particular region of said tomographic image based on a correlation coefficient obtained based on said autocorrelation process or said composite autocorrelation process.

37. An ultrasonic diagnostic method according to claim 26, wherein said step (2) comprises the step of reducing noise comprised in said time-series data.

38. An ultrasonic diagnostic method according to claim 26, wherein said step (1) comprises transmitting the ultrasonic wave along the longitudinal direction of the blood vessel to scan the blood vessel in the longitudinal direction of the blood vessel, while also scanning the blood vessel in a circumferential direction thereof, and step (2) comprises tracking the position of the location to be evaluated as it moves in the longitudinal direction of the blood vessel.

39. An ultrasonic diagnostic method comprising steps of:
   (1) transmitting an ultrasonic wave in a blood vessel, receiving a reflection of the ultrasonic wave, and producing a received signal representative of the received reflection;
   (2) calculating an instantaneous modulus of elasticity at a location to be evaluated in the blood vessel based on said received signal;

(3) analyzing a state of the location to be evaluated using time-series data of instantaneous moduli of elasticity which are calculated at a plurality of times in a chronological sequence; and (4) displaying an analyzed result produced in said step (3).

40. An ultrasonic diagnostic method according to claim 39, wherein said step (3) comprises the step of dividing said time-series data into a plurality of frequency components and analyzing the state of the location to be evaluated based on the intensity of a particular one of the frequency components.

41. An ultrasonic diagnostic method according to claim 40, wherein said step (3) comprises the step of judging that the proportion of a lipid component of a plaque formed in said blood vessel is lower as said intensity is higher.

42. An ultrasonic diagnostic method according to claim 39, wherein said step (3) comprises the step of analyzing the state of the location to be evaluated based on a phase lag of said time-series data.

43. An ultrasonic diagnostic method according to claim 42, wherein said step (3) comprises the step of judging that the proportion of a lipid component of a plaque formed in said blood vessel is higher as said phase lag is greater.

44. An ultrasonic diagnostic method according to claim 39, wherein said step (2) comprises the step of tracking the position of the location to be evaluated in the blood vessel according to an autocorrelation process or a composite autocorrelation process.

45. An ultrasonic diagnostic method according to claim 44, wherein said step (1) comprises the step of transmitting the ultrasonic wave while scanning the blood vessel in a circumferential direction thereof, and transmitting the ultrasonic wave while scanning the blood vessel in a longitudinal direction thereof.

46. An ultrasonic diagnostic method according to claim 45, wherein said tracking step allows tracking of the position of the location to be evaluated which moves in the longitudinal direction of the blood vessel.

47. An ultrasonic diagnostic method according to claim 39, wherein said step (4) comprises the step of displaying a tomographic image of the blood vessel based on said received signal and displaying the analyzed result over said tomographic image.

48. An ultrasonic diagnostic method according to claim 47, wherein said step (2) comprises the step of tracking the position of the location to be evaluated in the blood vessel according to an autocorrelation process or a composite autocorrelation process.

49. An ultrasonic diagnostic method according to claim 48, wherein said step (4) comprises the step of displaying said tomographic image with a change in the luminance of a particular region of said tomographic image based on a correlation coefficient obtained based on said autocorrelation process or said composite autocorrelation process.

50. An ultrasonic diagnostic method according to claim 39, wherein said step (2) comprises the step of reducing noise comprised in said time-series data.

51. An ultrasonic diagnostic method according to claim 39, wherein said step (2) comprises the step of calculating an absolute modulus of elasticity based on a blood pressure.

52. An ultrasonic diagnostic method according to claim 39, wherein said step (2) comprises the step of calculating a relative modulus of elasticity using a given reference point in said blood vessel as a point of reference.

53. An ultrasonic diagnostic method according to claim 39, wherein said step (1) comprises transmitting the ultrasonic wave along the longitudinal direction of the blood vessel to scan the blood vessel in the longitudinal direction of the blood vessel, while also scanning the blood vessel in a circumferential direction thereof, and step (2) comprises tracking the position of the location to be evaluated as it moves in the longitudinal direction of the blood vessel.

* * * * *